Figure 1:
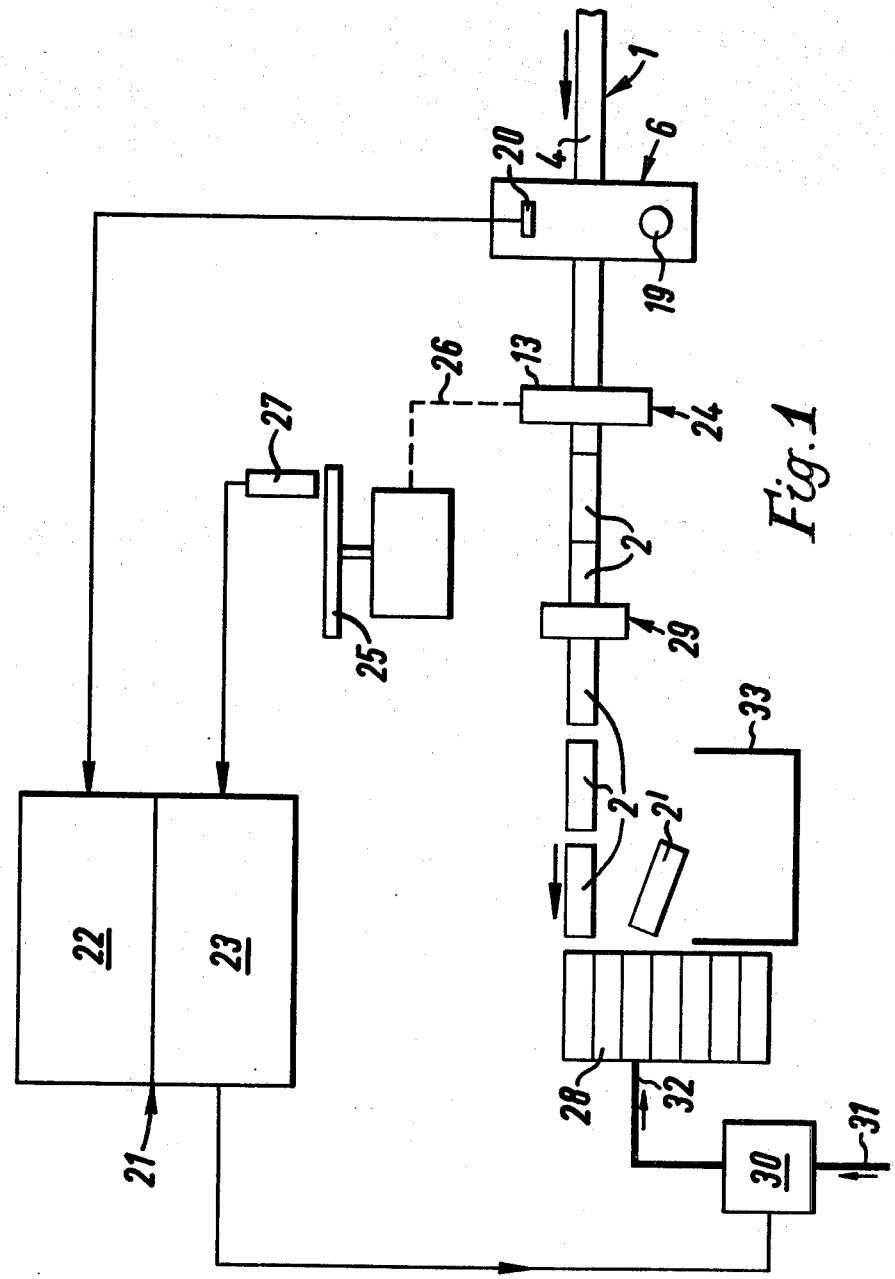

United States Patent [19]

Bryant

[11] 4,168,641

[45] Sep. 25, 1979

[54] FILTER ROD MANUFACTURE

[75] Inventor: Robert G. W. Bryant, Southampton, England

[73] Assignee: British-American Tobacco Company Limited, London, England

[21] Appl. No.: 859,012

[22] Filed: Dec. 9, 1977

[30] Foreign Application Priority Data

Nov. 14, 1976 [GB] United Kingdom ............... 52148/76

[51] Int. Cl.² ............................................. A24C 5/28
[52] U.S. Cl. ......................................... 83/80; 83/106;
83/365; 83/371; 83/444; 250/572
[58] Field of Search ..................... 83/80, 79, 106, 365, 83/371, 444; 250/572, 237 R

[56] References Cited

U.S. PATENT DOCUMENTS

| | | | |
|---|---|---|---|
| 3,093,020 | 6/1963 | Walsh | 83/106 |
| 3,264,916 | 8/1966 | Owen | 83/80 |
| 3,854,587 | 12/1974 | McLoughlin | 250/578 X |
| 4,001,579 | 1/1977 | Lebet et al. | 250/572 X |

Primary Examiner—J. M. Meister
Attorney, Agent, or Firm—Kane, Dalsimer, Kane, Sullivan & Kurucz

[57] ABSTRACT

The invention provides an arrangement for detecting faults in wrapped filter rod, for tobacco-smoke filtration, prior to its being cut into lengths, the arrangement comprises a light source and a light-sensitive receiver, for example a photo-transistor, in a housing provided with a rod guide which imposes on the rod a path between and spaced away from the said light source and receiver, a beam of light from the said source being projected through the said path of the rod to the receiver. Advantageously the housing bounds a cavity from which extraneous light is excluded and the light source and receiver are disposed behind respective transparent windows spaced away from the said rod path. The said receiver may be operatively connected to a system by which a faulty rod length detected is caused to be rejected after having been cut off from the rod.

9 Claims, 5 Drawing Figures

FILTER ROD MANUFACTURE

This invention concerns improvements relating to the manufacture of filter rods for tobacco smoke. In the manufacture of filter rods composed of two or more sections in a continuous operation it is particularly important that rod faults should be promptly and reliably detected.

Filter rods composed of two or more sections are commonly assembled with the aid of drum conveyors and are wrapped in paper to form a continuous rod which is then cut into required filter-rod lengths, generally lengths which are a multiple of the ultimate filter lengths. It is desirable to be able to detect filter-rod lengths which are faulty, particularly those in which a filter section is missing, leaving a void within the tubular wrap.

According to the invention, an arrangement for detecting faults in wrapped filter rod prior to its being cut into rod lengths comprises a light source and a light-sensitive receiver in a housing provided with a rod guide disposed to impose on the rod a path between and spaced away from the said light source and receiver, it being arranged that a beam of light from the said light source passes through the said path of the rod to the receiver. Preferably the light-sensitive receiver is a photo-transistor. Advantageously, the housing bounds a cavity from which extraneous light is excluded, the light source and receiver being disposed at walls of the housing on opposite sides of the said rod path.

The light source and receiver may be disposed behind respective transparent windows spaced away from the said rod path.

Generally the receiver will be operatively connected to a rejection system by which a faulty rod length detected is caused to be rejected subsequently to its having been cut off from the rod.

It has been proposed heretofore (German Patent Specification No. O.S. 2,451,760) that a monitoring device for a rod machine employed in the tobacco industry should be provided between a cut-off device, for severing the rod into individual articles, and a discharge conveyor for the articles, the monitoring device comprising a light source, a light sensitive receiver and a fixed article guide made of transparent material and the source and receiver being disposed so that light rays between them pass through the transparent material. This arrangement, described specifically in relation to cigarettes, although it is said to be applicable also to filter rods, would present certain difficulties in the latter case. The detection of a void in a tubular filter wrap involves different problems from the detection of the absence of cigarette rod. The monitoring of filter rod encounters difficulties with respect to dirt which are different from those, arising primarily from tobacco dust, sought to be overcome by the known arrangement. For instance, hot-melt adhesives commonly used to seal the paper wrap of filter rod would be liable to build up on the transparent guide and dust would then be likely to become embedded in the adhesive. Dust from carbon, say, in a filter section would be liable to abrade the transparent guide and impair its transparency. The present invention seeks to provide an arrangement free from such dangers.

Figure 2:
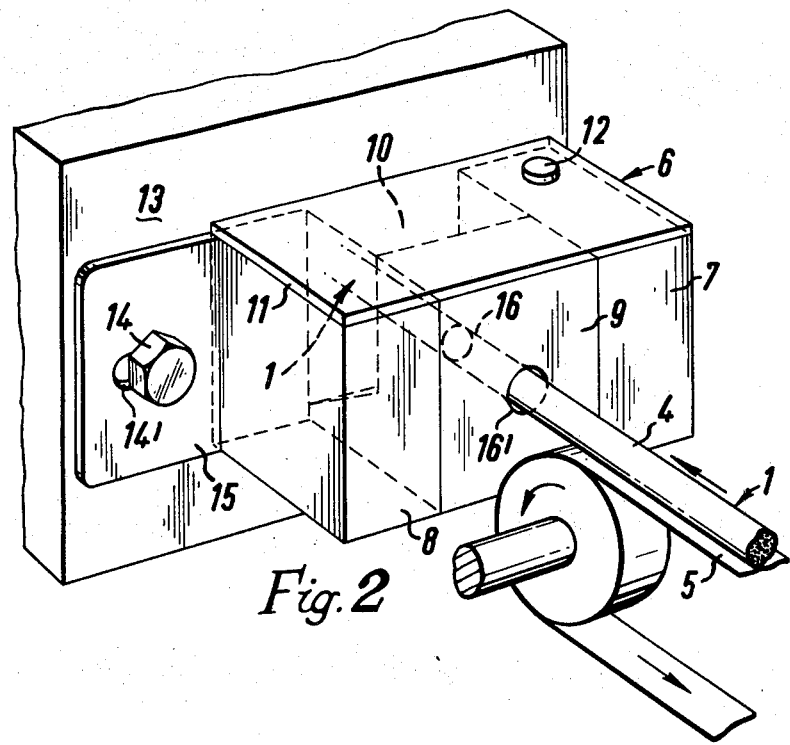
Figure 3:
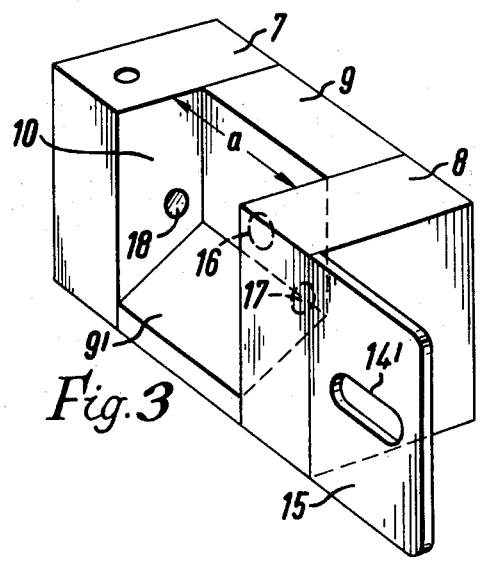
Figure 4:
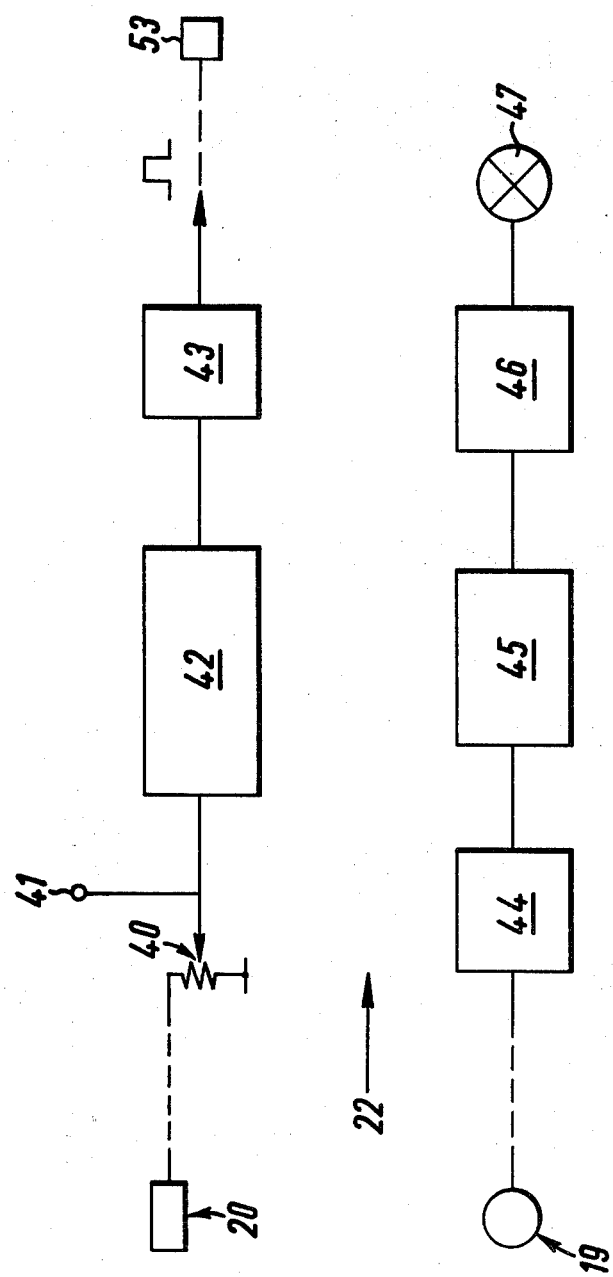
Figure 5:
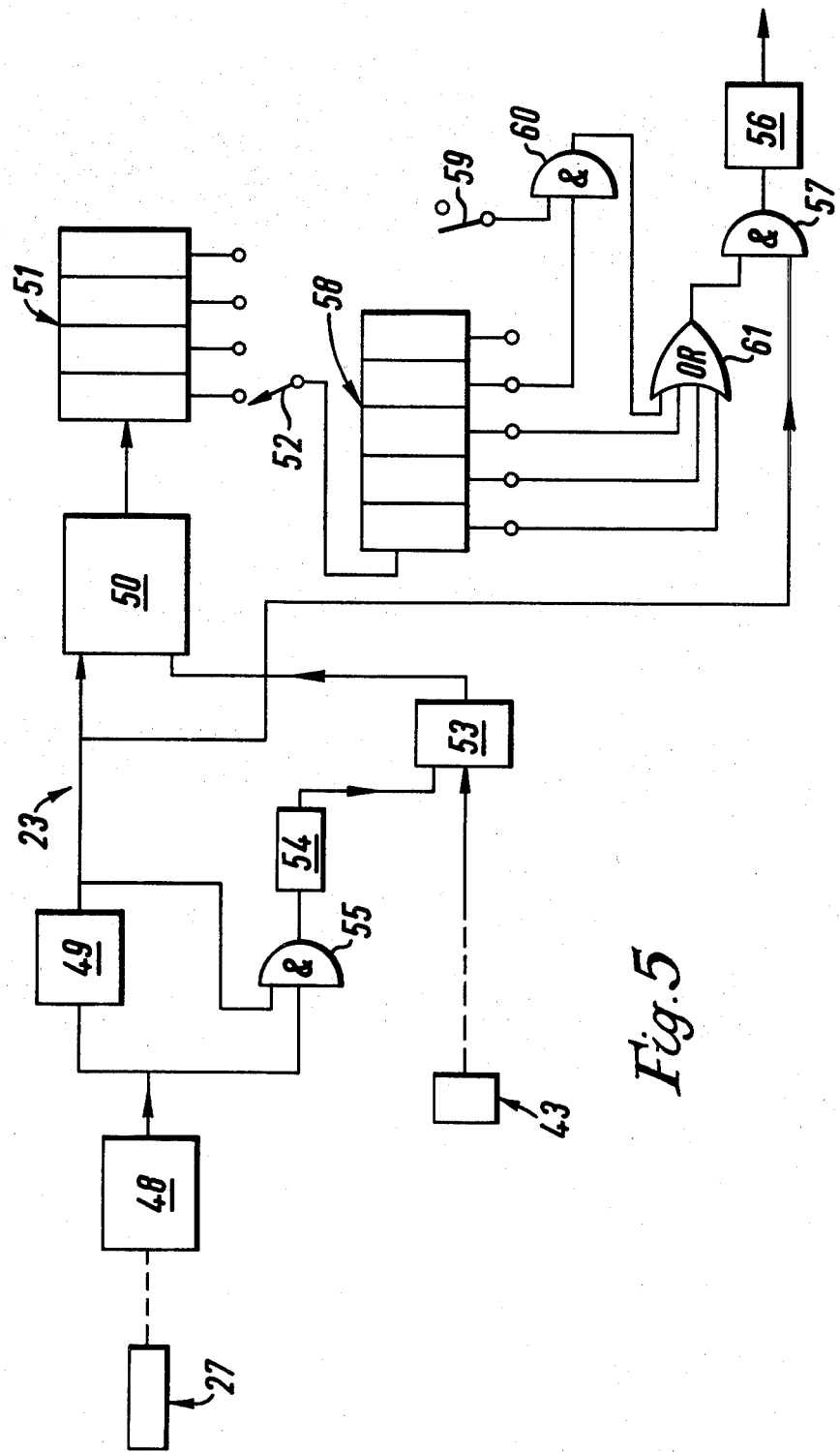

One embodiment of the invention will now be described by way of example with reference to the accompanying drawings, in which:

FIG. 1 is a purely diagrammatic representation illustrating a fault-detection arrangement in relation to the path of an assembled filter rod and to devices which operate upon the filter rod, FIG. 2 is a perspective view to a larger scale of a fault-detection device and immediately adjacent components as seen in the direction of entry of the rod into the device, FIG. 3 is a perspective view of the device as seen in the opposite direction, and FIGS. 4 and 5 are block-circuit diagrams for electrical circuitry.

Referring to FIG. 1 of the drawing, a filter rod 1 composed of two or more different types of filter sections assembled and enclosed within a tubular paper plug wrap 4 is delivered from a machine which has assembled and wrapped the sections in well-known manner. A suitable rod-producing machine for the purpose would be the Double Action Plug-Tube Combining Machine produced by Molins Limited of London. Of such a machine, the tape 5, which delivers the wrapped rod, is shown in FIG. 2.

The rod 1 is fed from the tape 5 to a fault-detection device 6 shown in greater detail in FIGS. 2 and 3. The device has two side casings 7, 8 fixed to an intermediate rod-entry block 9, suitably of aluminium, and forming a cavity 10 which is normally covered by a plate 11 removably or pivotably mounted on the casing 7 by a bolt 12 (FIG. 2). The block 9 has a sloping bottom 9' from which any debris collecting in the cavity 10 can be arranged to be discharged. The assembly 7, 8, 9 is mounted on one face of the adjacent wall of the guard box 13 of a cut-off device, hereinafter referred to, by means of a bolt 14 passing though a transversely elongated slot $14^1$ in a bracket 15 by which the assembly is supported. With the assembly so mounted and the cover 11 in place, substantially no extraneous light can penetrate into the cavity 10. The filter rod 1 enters the device through a guide hole 16 which has a diameter only slightly greater than that of the rod and of which the entry $16^1$ is radiused. The hole 16 affords accurate guidance of the rod 1 into the cavity 10, guidance being resumed on the other side of the cavity by the usual ledgers and guide tube of the cut-off device. The slot $14^1$ permits of adjustment for accurate transverse alignment of the hole 16 with the rod-guiding means in the box 13. The guidance imposes on the rod a predetermined path across the cavity.

At the sides of the cavity 10, the inner walls of the casings 7, 8 have aligned silica glass windows 17, 18 (FIG. 3). For a filter rod of substantially 8 mm diameter, the distance a between the outer surfaces of the windows is suitably 12.5 mm so that the said surfaces are spaced well away from the guided path of the rod. In FIGS. 2 and 3, the distance between the casings 7 and 8 and therefore the dimension a have been shown exaggerated for the sake of clarity. Located in the casing 8 behind the window 17 is a lamp 19 (FIG. 1) associated with a lens, preferably a lens-ended filament lamp (e.g. a 1.6 volt lamp) of known type, designed to project a narrow coherent beam across the cavity 10, through the central axis of the path of the rod 1, to the opposite window 18. Located in the casing 7 behind the window 18 is a photo-transistor 20, suitably of Darlington type, also provided with a lens. The intensity of the light emitted by the lamp 19 is sufficient, in the absence of a filter section in the passing filter rod, to activate the photo-transistor despite the presence of the tubular wrap 4, but insufficient for activating the photo-transistor as long as filter sections are present, in the wrap, between the two windows 17, 18. Thus the device is adapted to detect a void in the wrap.

Activation of the photo-transistor 20 is utilised to cause a "fault" signal to be transmitted to electronic control circuitry 21 (FIG. 1). This circuitry comprises a fault-monitoring section 22, to which the aforesaid "fault" signal is fed, and a section 23 comprising memory logic and timing circuits, and rejection-control means. The circuitry, which may comprise component circuits well known for similar purposes, serves, briefly, to memorise the position of a detected fault and to activate rod-length rejection means hereinafter referred to.

FIG. 1 shows also means for providing a train of signals synchronized with the operation of the cut-off device 24 whose guard box 13 has been previously mentioned. This means comprises a disc 25 driven synchronously with the cut-off device 24, as indicated by the broken line 26, at such speed as to make one revolution per cut. The disc serves to activate a sensor 27, for example a known photo-electric or electromagnetic sensor, once per cut and to transmit one signal per cut to the circuitry section 23.

By way of example, a suitable combination of component circuits in the circuitry 21 is illustrated in FIGS. 4 and 5. In this example, the section 22 includes a potentiometer 40 (FIG. 4) to which the "fault" signal from the photo-transistor 20 is supplied. The potentiometer, provided with a test point 41, permits of adjustment of the threshold level for fault detection. The potentiometer is followed by a presettable transistor-switched time-delay circuit 42 which, when actuated by a threshold-level signal, after a short preset delay necessary to inhibit rejection due to the detection of normal small gaps between filter elements, actuates a Schmitt trigger circuit 43. The circuit 43 delivers a formed pulse to the section 23.

As also shown in FIG. 4, the section 22 may include a circuit monitoring the lamp 19. Suitably this includes an element 44 which monitors the lamp current and is connected to a Schmitt trigger circuit 45 connected in turn to means 46 controlling flashing of a warning lamp 47 in the event of failure of the lamp 19.

The section 23 comprises logic circuits which control shift register circuits and the timing of an ejection system when a "fault" signal originating from the photo-transistor 20 is registered.

As shown in FIG. 5, the sensor 27 is connected, in the section 23, to the input of a Schmitt trigger element 48 which shapes the signal from the sensor so that a well-defined pulse is produced suitable for operating low-level logic circuits. The output of the element 48 is employed to control a monostable element 49 which delivers a constant-width pulse to provide a shift signal to a ($\div 4$) counter 50, in the form of a 4-bit shift register and shift register circuits 51 selectable by a manually operated switch 52 which is preset in dependance upon the length of the filter-rod lengths being produced. In this manner, the timing for the rejection of a faulty rod can be co-ordinated with the said length.

The formed pulse from the circuit 43 of the section 22 is supplied to and serves to prime a latch circuit 53 which is reset, once per revolution of the disc 15, by the signals from the sensor 27. For this resetting, the circuit 53 is connected through a delay circuit 54 to the output of an AND element 55 which has inputs connected respectively to the outputs of the trigger element 48 and the monostable element 49. The latch circuit 53 is connected to the shift register 51 via the counter 50, so that the said circuit can send a signal indicating a fault condition via the said counter to the said register.

The output of the register 51, preset for rod length as previously described, is supplied, possibly through a further shift register to be described, to a monostable element 56 by way of an AND element 57 to which the signal from the monostable element 49 is also supplied. The element 56 provides an electrical pulse, of constant width, which constitutes the output from the section 23 and serves to switch a power transistor (not shown) for actuating ejection means to be described.

For the rejection, use is made of a fluted drum 28 (FIG. 1) of a kind commonly used as a so-called deflector drum for transferring, to a catcher band, rod lengths which arrive in line from a spacing device and are received in the drum, one length per flute. For the present purpose, rod lengths 2 cut off by the device 24 and spaced apart by a spacing device 29 (FIG. 1) are similarly fed to the flutes of the drum 28. An electropneumatic valve 30 has its solenoid connected to the power transistor controlled by the monostable element 56. The valve 30 is connected to an air-delivery line 31 whose outlet at 32 is disposed in a fixed position to direct a pulse of compressed air along a flute of the drum 28 when the valve is opened. A filter-rod length 2' occupying that flute will then be ejected into a reject receptacle 33 or onto a conveyor.

In operation, as long as no faulty filter section is detected by the device 6, the rod 1 will pass through that device without activation of the photo-transistor 20, the circuitry 21 and the solenoid valve 30. The rod will be cut into lengths 2 by the cut-off device 24 and the lengths will be spaced apart by the device 29 and delivered individually to the flutes of the drum 28 from which they are in turn delivered to means for forwarding them in known manner, for example by a transverse conveyor belt, for further processing, generally including further subdivision of the lengths 2.

In the event of a fault being detected, the rod continues to pass through the devices 24 and 29 and the filter-rod lengths 2 continue to be delivered to the drum 28, but, on the detection of the faulty length, a "fault" signal is transmitted to the monitoring section 22 which, as previously described passes an activating signal to the section 23. After an interval of time corresponding to the time required for the rod length containing the fault to progress to the drum flute opposite the air outlet 32, the monostable element 56 delivers a voltage pulse to the power transistor which furnishes a current pulse to energise and open the valve 30, so that the faulty length, at this time in the said drum flute, is ejected therefrom.

If required, provision may be made for satisfying different requirements as to the ejection of a rod length or lengths in addition to the length actually detected as faulty. For example, provision may be made for ejecting also a length preceding the faulty length and a length following the faulty length or the preceding length and two following lengths. Such requirements may be catered for by setting a logic circuit in the circuitry section 23 so that pulses of air are also delivered at times when the said further length or lengths are opposite the outlet 32 of the line 31. For this purpose, with the circuitry described above, there is provided, between the register 51 and the monostable element 56 for providing the output pulse via the output transistor, a further shift register 58 which can be preset by a manual switch 59 to preselect a required combination of rod lengths to be ejected. In this case, the register 58 and the switch 59 are connected by way of AND and OR elements 60 and 61 to the AND element 57 whose other input is from the monostable element 49.

Electronic counting means may be linked to the circuitry 21 for counting the number of rejected lengths and, if required, the number of accepted lengths in a particular machine run. For this purpose, signals are obtained from the section 23 for operating counters (not shown) for providing totals of rejected and accepted lengths. The counter for rejected lengths is advanced when the valve 30 operates. That for accepted lengths is advanced when no fault signal coincides with a signal from the sensor 27.

In some cases, particularly when the present invention is applied in conjunction with an existing rod-forming machine, existing components of that machine may conveniently be utilised as or adapted for the components 24 and 29 and possibly, the drum 28.

I claim:

1. An arrangement for detecting voids in wrapped filter rod for tobacco-smoke filtration, prior to its being cut into lengths, comprising a light source and a light-sensitive receiver in a housing provided with a rod guide disposed to impose on the rod a path between the light source and receiver, it being arranged that a beam of light from the light source passes, through the path of the rod, to the receiver, the rod path imposed by the guide being spaced substantially away from the light source and receiver whereby impairment of the light transmission therebetween due to fouling and abrasion by filter-dust particles is minimized.

2. An arrangement according to claim 1, wherein the housing bounds a cavity from which extraneous light is excluded, the said light source and receiver being disposed at walls of the housing on opposite sides of and spaced away from the said rod path.

3. An arrangement according to claim 1, wherein the said light source and receiver are disposed behind respective transparent windows spaced away from the said rod path.

4. An arrangement according to claim 1, wherein the said receiver is a photo-transistor.

5. An arrangement according to claim 1, wherein cut-off means is provided for cutting the rod into rod lengths and the said receiver is operatively connected to a rejection system by which a faulty rod length detected as having a void is caused to be rejected subsequently to its having been cut off from the rod.

6. An arrangement according to claim 5, wherein the said system comprises electronic circuitry including first, void-monitoring, means to the input of which the said receiver is connected and second means connected to the first means and comprising memory and logic circuits, timing means and an output circuit controlling means for causing rejection of a rod length having a void.

7. An arrangement according to claim 5, wherein means providing time-signals in synchronism with the operation of the said cut-off device is connected to the said system.

8. An arrangement according to claim 5, comprising an electropneumatic valve having its activating circuit connected to the said system and arranged to reject a rod length having a void pneumatically.

9. An arrangement according to claim 5, comprising a fluted drum and means by which the rod lengths are individually delivered to the drum flutes and means by which rod lengths having voids are rejected from the said flutes.

* * * * *